United States Patent [19]

Nishioka

[11] Patent Number: 5,449,754
[45] Date of Patent: Sep. 12, 1995

[54] GENERATION OF COMBINATORIAL LIBRARIES

[75] Inventor: Gary M. Nishioka, Pataskala, Ohio

[73] Assignee: H & N Instruments, Inc., Newark, Ohio

[21] Appl. No.: 231,494

[22] Filed: Apr. 22, 1994

Related U.S. Application Data

[63] Continuation-in-part of Ser. No. 8,131, Jan. 25, 1993, Pat. No. 5,318,679, which is a continuation-in-part of Ser. No. 741,771, Aug. 7, 1991, abandoned.

[51] Int. Cl.⁶ .............................................. C07K 1/00
[52] U.S. Cl. ..................................................... 530/334
[58] Field of Search ................. 436/518, 527; 530/334

[56] References Cited

U.S. PATENT DOCUMENTS

| | | | |
|---|---|---|---|
| 4,704,583 | 11/1987 | Gould | 330/4.3 |
| 4,746,201 | 5/1988 | Gould | 350/394 |
| 4,816,513 | 3/1989 | Bridgham et al. | 425/54.11 |
| 5,143,854 | 9/1992 | Pirrung et al. | 436/518 |
| 5,258,454 | 11/1993 | Berg et al. | 525/54.11 |
| 5,288,514 | 2/1994 | Ellman | 427/2 |

OTHER PUBLICATIONS

Solid Phase Peptide Synthesis. I. The Synthesis of a Tetrapeptide, by R. B. Merrifield, "Merrifield" J. Am. Chem. Soc. (1963) 85:2149–2154, QUI Am 35j.
"Single—Domain Antibodies Promise New Chemical, Medical Applications" C&E News, Nov. 20, 1989.
"Lights! Camera! Print It! Laser Printer Technology Explained" Alfred Poor (PC Magazine, Nov. 14, 1989, pp. 168–169.)
"Light-Directed, Spatially Addressable Parallel Chemical Snythesis" S. Fodor, et al., Science, 251, 767 (1991).
"Photoremovable Protecting Groups in Organic Synthesis" V. N. Pullai, Synthesis, 1 (1980).
A. Patchornik, et al., JACS, 92, 6333 (1970) Photosensitive Protecting Groups.
"Binding activities of a repertoire of single immunoglobulin variable domains secreted from *Escherichia coli*" E. S. Ward, et al., Nature, vol. 341, 544 (1989).
"Peptides, Structure and Function" edited by C. M. Deber, V. J. Hruby, and K. D. Kopple, Pierce Chemical Co., Rockford, Ill., (1985).
"Searching for Peptide Ligands with an Epitope Library" J. K. Scott and G. P. Smith, Science, vol. 249, 386 (1990).
"Random Peptide Libraries: A Source of Specific Protein Binding Molecules" J. J. Devlin, L. C. Panganiban, and P. E. Devlin, Science, vol. 249, 404 (1990).
"Laser Recording And Image-Quality Evaluation" K. Minoura, et al., SPIE, vol. 1254, 24 (1990).
"A laser scanning optical system for high-resolution laser printer" T. Maruyama, et al., SPIE, vol. 1254, 54 (1990).
"Immunogenicity of Synthetic Peptides Corresponding to Flexible and Antibody–accessible Segments of Mouse Lactate Dehydrogenase (LDH)-C₄*"H. Hogrefe, P. Kaumaya, and E. Goldberg, J. Biol. Chem., vol. 264, 10513 (1989).
"Peptide engineering of protein topographic determinants for vaccines" P. Kaumaya, et al., in "Peptides 1990", ESCOM Science B.V. (1991).
"Synthesis and Biophysical Characterization of Engineered Topographic Immunogenic Determinants with aa Topology" P. Kaumaya et al., Biochemistry, 29, 13 (1990).
Internet memorandum: David B. Wallace, "Fluid Microdispensing In Genosensor Development", Oct. 29–30, 1993, one page.

*Primary Examiner*—John Niebling
*Assistant Examiner*—C. Delacroix-Muirheid
*Attorney, Agent, or Firm*—Sidney W. Millard

[57] ABSTRACT

Ink-jet printing technology is applied to the creation of multi unit chemical compound libraries. Ink-jet type nozzles are used to inject multiple droplets onto the surface an appropriate support, such droplets consisting of solutions containing units of the chemical compound that will attach to the support surface. Droplets are then injected, by such nozzles, onto the support attached unit droplets that contain units that will attach to such support attached units. The second step is repeated to create multiple varying unit chemical compounds. Ink-jet printing technology allows the deposition of small droplets that do not overlap or splatter. The system is particularly useful in the creation of libraries of multiple peptide compounds where the units are amino acids.

8 Claims, 1 Drawing Sheet

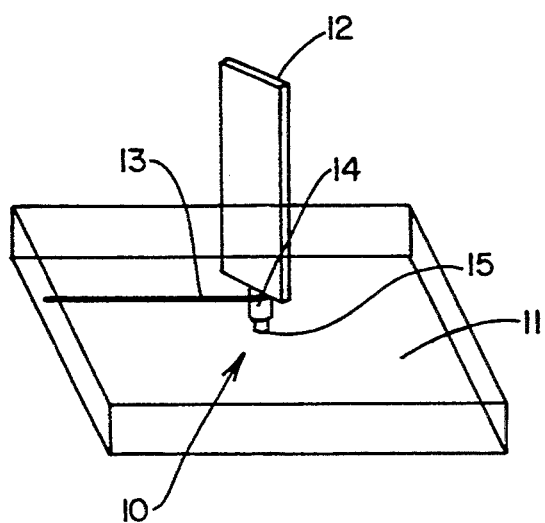

GENERATION OF COMBINATORIAL LIBRARIES

This is a continuation-in-part of application Ser. No. 08/008,131, filed Jan. 25, 1993, now U.S. Pat. No. 5,318,679 which is a continuation-in-part of application Ser. No. 07/741,771, filed Aug. 7, 1991, now abandoned.

FIELD OF THE INVENTION

The present invention is an improved method of making sequenced chemical compounds through the application of ink-jet printer technology to the synthesis of combinatorial arrays and particularly to the combination of ink-jet printer technology and solid phase peptide synthesis.

BACKGROUND OF THE INVENTION

Recently, so-called combinatorial methods have gained great interest as a brute force method for finding desirable compounds. These methods involve creating libraries of related compounds, for example, all possible hexapeptides. The interaction of an antigen with the library is then measured. For example, those peptides that strongly bind to the antigen exhibit molecular recognition of the antigen. Thus, combinatorial properties are comparable with the goal of finding a particular molecule with the desired tailored properties.

A variety of combinatorial approaches have been described. Biological methods involve creating a series of bacteriophages, each with a different peptide on its surface (see Scott, J. K., and Smith, G. P., *Science*, (1990)249, 386 and Devlin, J. J., Panganiban, L. C., and Devlin, P. E., *Science*, (1990) 249, 404.) Phages binding to the desired antigen are recovered; by sequencing the DNA of these phages the peptide sequences on their surfaces are determined. These peptides are those that can confer molecular recognition of the antigen.

Chemical methods involve the synthesis of different peptides, usually spatially separated on solid supports. One approach is the synthesis of millions of peptides, each on a separate resin bead (see Lam, K. S. et al., *Nature* (1991) 354, 82.) An alternative to spatially separated libraries is the use of encoded combinatorial libraries, in which each peptide sequence is labeled by an appended genetic tag (see Brenner, S., and Lerner, R. A., *Proc. Natl. Acad. Sci. U.S.A.*, 89, 5381).

Fodor and coworkers recently described a novel method for synthesizing large numbers of peptides bound to a solid support, by combining the techniques of solid phase peptide synthesis, photolabile protection, and photolithography (see Fodor, S. P. A., *Science*, (1991) 251,767). Their method, called light activated parallel chemical synthesis, makes possible the systematic synthesis and investigation of a large number of different peptides. Its principal advantage is the ease with which any peptide can be decoded. Merely identifying the spatial coordinates of the desired peptide is sufficient to determine its sequence. However, the technique has some serious disadvantages. The method uses amino acids with photolabile protecting groups. Peptide synthesis involves a new set of chemistries; achieving high yields of the desired peptides will require significant effort. More importantly, the use of photolithographic masks combined with solid phase synthesis is inherently labor intensive, and requires specialized skills and equipment. It is generally conceded that the establishment of this method as a routine is simply not possible, since it involves large investments in both equipment and personnel (see Jung, G., and Beck Sickinger, A. G., *Angewandte Chemie*,(1992) 31,367).

U.S. patent application Ser. No. 08/008,131, filed Jan. 25, 1993 entitled SYNTHESIS OF CHAIN CHEMICAL COMPOUNDS, describes a related technique (to the Fodor technology described above) which eliminates the drawbacks associated with the use of photographic masks by substituting laser scanning for the photolithographic masking step. By this method portions of a photolabile protected amino acid surface are deprotected by a laser printer beam (such as a 5 mW HeCd laser, 3250 Å). Radiation of wavelengths longer than 3200 Å will not damage the most sensitive amino acid, tryptophan. Control of the spatial coordinates which the laser beam deprotects is accomplished by reflecting the laser beam from a spinning mirror, and employing a shutter to block the beam from the surface when desired. The support is moved perpendicular to the scan lines using a precision optical translator. (see also Nishioka, G. M., "Programmable Laser Activated Parallel Synthesis",[1992] NSF Phase I SBIR Final Report under contract ISI-9160637).

The efficacy of the above described laser printer-photolabile protected amino acids has been demonstrated. Also a 1600 site array was synthesized, simply by scanning 40 times in perpendicular directions. Finally, variations of a simple peptide were synthesized in separate scan lines and characterized by antibody adsorption.

The above described system (now call PROLAPS for Programmable Laser Activated Parallel Synthesis) makes possible the automated synthesis of immobilized peptides libraries requiring little specialized skill on the part of the user. However, PROLAPS retains the disadvantage of using amino acids with photolabile protecting groups. It also retains the disadvantage of requiring 20 separate deprotection steps for each position in a peptide that is to be exhaustively varied. For example, the synthesis of all possible hexapeptides requires 20×6=120 separate deprotection, wash, and coupling steps. If each cycle requires 1 hour, then 5 days are required to synthesize the array.

SUMMARY OF THE INVENTION

A method and instrument have now been devised with the ability to synthesize large peptide arrays that overcomes the aforementioned difficulties. This method called SCAMP (Synthesis of Combinatorial Arrays by Microjet Printing), combines ink-jet printer technology and solid phase chemical synthesis. This method has been found to be particularly amenable to the synthesis of solid phase peptides.

In accordance with this invention a support, such as an aminated glass slide, filter or membrane, is placed on a vibration-free platform. A print head is mounted to precision xy translators above the sample. The print head scans the sample, depositing small droplets (typically 0.1 μg) of coupling solution onto programmed sites on the support. The activated coupling solutions may be similar to those used in commercial peptide synthesizers and will result in a protected amino acid binding to the support.

The print head will preferably contain a minimum of 20 orifices, so that at least 20 different solutions can be injected onto the support in one pass. Typically, each orifice will inject a particular amino acid onto the support.

After the first scan, a single layer of amino acids will be bound to the support at programmed sites. The support is then washed, deprotected and then washed again. The scan, wash, and deprotection steps are repeated as often as desired, resulting in the synthesis of immobilized peptides at the programmed sites. The final step is removal of side-chain blocking groups.

BRIEF DESCRIPTION OF THE DRAWING

The figure is an illustrative schematic representation of a droplet generator (an ink-jet printer device) which may be used to accomplish the method of the present invention.

DETAILED DESCRIPTION OF THE PREFERRED EMBODIMENTS

An example of the synthesis of all possible hexapeptides would be as follows: In the first round each amino acid is bound to 3,200,000 sites ($3,200,000 \times 20 = 64$ million $= 20^6$). In the second round, each amino acid is bound to 1/20 of each of the original first round sites ($160,000 \times 20 = 3,200,000$). In the third round each amino acid is bound to 1/20 of each of the second round sites ($8000 \times 20 \times 20 = 3,200,000$). The fourth, fifth, and sixth rounds proceed similarly, so that at the end of the synthesis there are 64 million sites, each containing a different hexapeptide.

Synthesis of megapeptide arrays is reasonable using SCAMP. A low-cost ink jet printer can deposit over 7,000,000 dots on a page in less than a minute. If the dot size is reduced to 10 $\mu$m, an 8,000 by 8,000 grid will be 8 cm on a side which is a reasonable size for use in the present invention.

Registry of the droplets is perhaps the most critical parameter affecting SCAMP. Droplets must impinge on the same site in successive rounds for the method to be successful. Errors in centering of successive droplets will result in the formation of deletion peptides at the edges of the site.

To achieve satisfactory registry in SCAMP precision optical translators can be used to position the print head. These are reproducible to 0.1 $\mu$m. In addition, surface tension gradients will tend to center the deposited droplets if the surrounding surface is of a lower energy than the site. A glass slide aminated using an aminosilane will have a low surface energy; deposition of the relatively polar amino acids will raise the surface energy of the site.

The work of adhesion and cohesion of the droplet in relation to its kinetic energy determines whether the droplet "splatters" on the surface, or is deposited as a uniform drop. The kinetic energy of a droplet of mass 0.1 $\mu$g traveling at 5 m/sec is $2.5 \times 10^{-5}$ ergs. The work of adhesion of the droplet to a surface is well known to be:

$$Wa = \sigma(1 + \cos \theta)$$

where,

Wa = work of adhesion = work required to remove the drop from the surface per unit contact area,
$\sigma$ = surface tension of the drop, and
$\theta$ = contact angle of the drop oil the surface.

A droplet contacting the surface with $\theta = 60°$ with a circular contact radius of 25 $\mu$m will require about $7.5 \times 10^{-4}$ ergs for removal, or 30 times the kinetic energy of the drop. Therefore, droplets will contact and stick to the surface. A similar analysis comparing the work of cohesion and kinetic energy leads to similar results, indicating that the droplet will not splatter but will remain as a single splatter. (See Ross, S. and Morrison, I., "Colloidal Systems and Interfaces", Wiley, N.Y.[1988]).

The print head design is similar to those developed for piezoelectric drop-on-demand ink jet printers (see Bupara, S., and Howkins, S., SPIE Proc., 1079[1989],400). As shown in the drawing, when the print head 10 is over the desired site on a substrate 11, a driver circuit sends a short pulse (typically 5 $\mu$s at 100 V) to the piezoelectric element 12. The element undergoes a sudden change in volume, compressing the solution delivered through supply duct 13 into compression chamber 14, and causing a single droplet to be ejected from the nozzle 15. Typically, a droplet of mass 0.1 $\mu$g is ejected, with a velocity of 5 m/sec, creating a 50 $\mu$m spot (see Onishi, H., et al., Jpn Kokai 04,235,042[1992]).

Advantages of SCAMP include:

1. Standard chemistries. SCAMP can use well-established chemistries such as t-BOC or FMOC protecting groups. The large body of experience concerning the solid phase synthesis of peptides can be exploited in the development of SCAMP.
2. Efficient synthesis methodology. SCAMP features the ability to deposit different amino acids in one pass. Thus, in generating a combinatorial library all 20 amino acids can be bound in one cycle. Exhaustively varying 6 positions in a peptide requires 6 cycles, as opposed to 120 cycles in light activated methods.
3. Programmable synthetic schemes. The spatial arrangement of synthesis sites is easily established by controlling which solution is deposited at each site.
4. Convenient synthesis methodology. SCAMP permits the synthesis of immobilized peptide arrays to be completely automated.
5. Low cost. SCAMP uses low cost components, so a commercial instrument is readily affordable by most research laboratories.

SCAMP makes possible the synthesis of peptide arrays containing millions (or even more) different peptides. It should be emphasized that SCAMP is not limited to the synthesis of short peptides. Any length of peptide (or other chain chemical compound or molecule) can be examined; the limitation is the number of positions that can be exhaustively analyzed. SCAMP is not limited to the examination of short linear peptides, which in general are poor immunogens, generating antibodies of low affinity for the native protein. The sequence diversity using SCAMP can be exploited in the synthesis of peptide secondary and tertiary structures, to yield optimal molecular recognition.

While continuous determinants are composed of sequential residues in the peptide chain, discontinuous determinants consist of residues from different parts of the sequence, brought together by the folding of the peptide chain into its three dimensional structure. Investigation of discontinuous determinants may also be studied by SCAMP. For example, a peptide array can be synthesized by immobilizing a base sequence, varying the next three members, adding a "spacer" sequence, then varying three more members.

SCAMP offers significant advantages over the use of epitope libraries. Epitope libraries produce a large number of random short peptides. SCAMP can produce a large number of systematically varied long peptides. SCAMP also offers the ability to introduce variations into engineered peptide structures. SCAMP may ultimately be experimentally simpler. Finally, the representation of a protein/peptide interaction as a "map" is inherent to SCAMP and may aid visualization of this interaction.

Among the many benefits of available megapeptide arrays is that such arrays will aid in the design and synthesis of a wide variety diagnostic and therapeutic agents.

EXAMPLE

As an illustrative example of the process and apparatus of the present invention a piezoelectric ink-jet head (Epson Stylus 800) is mounted on a precision xy translator (New England Affiliated Technologies). Coupling solutions are loaded into the ink reservoir by hand. The Epson Stylus 800 print head contains 48 nozzles which are connected to a common reservoir (see *Printers Buyer's Guide and Handbook*, No. 10, Autumn 1993). In the example only one nozzle is used, however a head can be designed in which each nozzle is connected to a separate reservoir.

The print head is mounted over the support, which is an aminated glass slide or membrane. The support is placed on a stable platform at an angle from the horizontal to facilitate washing. The print head, support, and platform are positioned within a glass enclosure to reduce evaporation of the deposited droplets from the support. The entire assembly is placed on a vibration table (Peabody Noise Control).

A driver circuit controlled by a computer sends a pulse of controlled width ($\mu$sec) and height (volts) to the piezoelectric pump each time a droplet is to be ejected. The computer controls droplet ejection and movement of the xy translator so that droplets are placed at precisely determined locations on the support.

A protocol for peptide synthesis follows standard procedures employed in commercial peptide synthesizers (see Biosearch 9600 *Peptide Synthesizer Operator's Guide*). The major steps for synthesis using the acid-labile t-BOC protecting groups are given below. The protocol can also use a base-labile protecting group such as FMOC.

1. A glass slide is aminated by withdrawal from a 0.1% aminopropyltriethoxysilane in 95% ethanol solution at a rate of 250 $\mu$m/sec, and curing at 110° C. for 20 minutes.

2. The support is placed in the sample chamber, and washed with dichloromethane (DCM) and dimethylformamide (DMF).

3. An activated solution of a hydroxybenzotriazole (HOBt) ester of a t-butyloxycarbonyl (t-BOC) amino-protected amino acid is placed in the print head reservoir. These are formed by dissolving equimolar quantities of t-BOC amino acid, HOBt, benzotriazolyl-n-oxy-tris(dimethylamino)-phosphonium hexafluorophosphate (BOP), and N-methylmorpholine in DMF.

4. The print head deposits the coupling solution onto selected sites on the support.

5. Steps 3 and 4 are repeated as required. Step 5 will not be necessary when a print head with multiple reservoirs is added. The coupling takes 2 hours at room temperature.

6. The support is washed with DMF and methylene chloride acetic anhydride-triethyl amine-DCM solution to react free amines, and DMF and methylene chloride.

7. Deprotection is accomplished by washing the support with Trifluoracetic acid (TFA)-Indole-DCM solution.

8. Steps 3–7 are repeated as required.

9. The sample is washed at the end of the synthesis with trimethylsilyl trifluoromethanesulfonate-TFA-anisole solution (DEPRO kit, Sigma) to remove side-claim blocking groups.

Having thus described the apparatus and procedural steps for carrying out the invention, it will be clear to those having ordinary skill in the art, that various modifications may be made in the apparatus and the procedural steps without departing from the inventive concept. It is not intended that the words used in the specification to describe the invention, nor the drawings illustrating the same, be limiting on the invention. Rather it is intended that the invention be limited only by the scope of the appended claims.

I claim:

1. A method of making chemical compounds of preselected varying sequenced chemical units attached to the surface of a solid support comprising:
   a) injecting droplets of a first liquid solution containing one of said units that is disposed to attach to said surface from nozzles constructed in the manner of an ink-jet printing head positioned to deposit said droplets onto said surface in separate selective locations on said surface so that such units attach to the surface of said support; and
   b) injecting droplets of a second liquid solution containing one of said units that is disposed to attach to the units of said first liquid coupling solution from said nozzles positioned to cause said second droplets to impinge onto the selective locations so that the units of said second liquid attach to the units of said first liquid coupling solution attached to said support.

2. The method of claim 1 including:
   c) injecting droplets of a third liquid solution containing one of said units that is disposed to attach to the units of said first or second liquid solution from said nozzles position to cause said droplets to impinge on preselected droplets of said second liquid solution droplets so that the units of said third liquid attach to the units of said first or second liquid solutions.

3. The method of claim 2 wherein step c) is repeated with solutions containing varying preselected units disposed to attach to the units of one or more of the preceding injected solutions to create multiple unit chemical compounds.

4. The method of claim 1 wherein the support in step a) is sequentially moved relative to said nozzles and droplets of said first liquid coupling solution are injected onto said surface in multiple separate selective locations prior to step b) and wherein said support in step b) is sequentially moved relative to said nozzles so that droplets of said second liquid coupling solutions are injected to impinge onto the droplets of said of said first liquid solution in such multiple separate selective locations.

5. The method of claim 4 including:
   d) sequentially moving the support, relative to said nozzles and injecting droplets of a third liquid solution containing one of said units that: are disposed to attach to the units of said first or second liquid solution to impinge onto the units of said preselected droplets of said first or second liquid solutions in such multiple separate selective locations.

6. The method of claim 5 wherein step d) is repeated with solutions containing varying preselected units disposed to attach to the units of one or more of the preceding injected solutions to create multiple unit chemical compounds.

7. The method of claim 6 wherein, said chemical compounds are peptides and said unit are amino acids.

8. The method of claim 7 wherein said printing head contains a minimum of 20 nozzle orifices and each orifice is disposed to inject separate preselected amino acid units onto the support.

* * * * *